(12) United States Patent
Johansen (10) Patent No.: US 6,945,095 B2
(45) Date of Patent: Sep. 20, 2005

(54) NON-INTRUSIVE MULTIPHASE FLOW METER

(75) Inventor: Espen S. Johansen, Houston, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 0 days.

(21) Appl. No.: 10/348,040

(22) Filed: Jan. 21, 2003

(65) Prior Publication Data

US 2004/0139791 A1 Jul. 22, 2004

(51) Int. Cl.$^7$ .......................... G01N 33/20; G01N 37/00
(52) U.S. Cl. ...................................................... 73/61.45
(58) Field of Search ................. 73/861.18, 861.25, 73/861.26, 861.27, 861.28, 861.29, 861.31, 19.01, 19.05, 19.1, 61.41, 61.43, 61.46, 61.47, 152.08, 152.18, 152.42, 861.23; 200/81.4, 83 R, 83 Q (56) References Cited

U.S. PATENT DOCUMENTS

| | | | | |
|---|---|---|---|---|
| 3,780,577 A | * | 12/1973 | Brown ...................... | 73/861.28 |
| 3,906,791 A | * | 9/1975 | Lynnworth ............... | 73/861.29 |
| 4,574,643 A | * | 3/1986 | Scott et al. ................. | 327/104 |
| 4,680,957 A | * | 7/1987 | Dodd ......................... | 73/54.04 |
| 4,776,210 A | * | 10/1988 | Baillie et al. ............. | 73/861.04 |
| 4,856,344 A | * | 8/1989 | Hunt ......................... | 73/861.04 |
| 5,040,415 A | | 8/1991 | Barkhoudarian | |
| 5,224,372 A | * | 7/1993 | Kolpak ...................... | 73/19.03 |
| 5,317,909 A | * | 6/1994 | Yamada et al. ............ | 73/118.1 |
| 5,415,048 A | * | 5/1995 | Diatschenko et al. .... | 73/861.04 |
| 5,501,099 A | * | 3/1996 | Whorff ...................... | 73/29.01 |
| 5,719,329 A | | 2/1998 | Jepson et al. | |
| 5,803,056 A | * | 9/1998 | Cook et al. ................ | 123/520 |
| 5,892,860 A | | 4/1999 | Maron et al. .............. | 385/12 |
| 6,233,374 B1 | | 5/2001 | Ogle et al. ................. | 385/13 |
| 6,286,360 B1 | | 9/2001 | Drzewiecki | |
| 6,351,987 B1 | | 3/2002 | Winston et al. ............ | 73/53.01 |
| 6,354,147 B1 | * | 3/2002 | Gysling et al. ............ | 73/61.79 |
| 6,463,813 B1 | | 10/2002 | Gysling .................... | 73/862.59 |
| 6,502,465 B1 | | 1/2003 | Vedapuri et al. | |
| 6,651,514 B2 | | 11/2003 | Zanker | |
| 6,655,221 B1 | * | 12/2003 | Aspelund et al. ......... | 73/861.04 |
| 2001/0035312 A1 | * | 11/2001 | Han et al. .................. | 181/115 |
| 2002/0064331 A1 | * | 5/2002 | Davis et al. ................ | 385/12 |
| 2002/0152802 A1 | | 10/2002 | Gysling et al. | |
| 2003/0066359 A1 | * | 4/2003 | Gysling et al. ........... | 73/861.23 |
| 2004/0049358 A1 | * | 3/2004 | Cook et al. ................ | 702/45 |

FOREIGN PATENT DOCUMENTS

WO WO 02/48705 6/2002

OTHER PUBLICATIONS

Kragas, et al., "Downhole Fiber–Optic Multiphase Flow-meter: Design, Operating Principle, and Testing", Society of Petroleum Engineers, SPE Annual Technical Conference and Exhibition, Sep.–Oct. 2000.

U.K. Search Report, Application No. GB0401195.3, dated May 31, 2004.

U.S. Appl. No. 10/342,052, filed Jan. 14, 2003, entitled "Phase Flow Measurement in Pipes Using a Density Meter".

* cited by examiner

*Primary Examiner*—Charles Garber
(74) *Attorney, Agent, or Firm*—Moser, Patterson & Sheridan, L.L.P.

(57) ABSTRACT

Embodiments of the present invention generally provide methods, apparatus, and systems for determining void fractions of individual phase components of a multiphase mixture. The void fractions may be determined based on measured parameters of the mixture as a whole, such as differential pressure, bulk velocity of the mixture and speed of sound in the mixture. According to some embodiments, the mixture parameters may be measured using non-intrusive fiber optic based sensors. Various other parameters may also be derived from the void fractions, such as individual phase flow rates, liquid holdup and watercut parameters (for oil and gas mixtures).

36 Claims, 9 Drawing Sheets

NON-INTRUSIVE MULTIPHASE FLOW METER

BACKGROUND OF THE INVENTION

1. Field of the Invention

Embodiments of the present invention generally relate to downhole production operations and particularly to measuring volumetric fractions of individual phases of a multiphase mixture.

2. Description of the Related Art

Producing oil and gas wells typically provide a multiphase mixture of oil, gas, and water. Real-time, downhole flow data regarding the mixture (e.g., flow rate of the mixture, individual phase flow rates and fractional phase volumes, also referred to as "void fractions") is widely acknowledged to be of significant value for production optimization. This is particularly the case for high-cost deepwater developments and in complex multi-lateral wells. Downhole flow data may be utilized in various production operations.

As an example, in multi-zone completions, downhole flow data can be used to allocate production from individual zones. This can be achieved either with flow data gathered above each producing zone or with flow data gathered between each producing zone (using total flow measured at the surface) to obtain the contribution of the uppermost zone. As another example, flow data gathered from one or more locations along a lateral section of a horizontal well can help identify which parts of the lateral section are contributing to flow and may help locate a production anomaly, such as a water or gas breakthrough, thus allowing localized well stimulation or other well treatments to be performed to increase well productivity.

Real-time downhole flow rate data may also allow determination of a well productivity index at any time without need for intervention, determination of contribution of multiple zones in commingled production. Further, real-time downhole flow data may reduce the need for surface well tests and eliminate the need for associated equipment, such as a surface test separator, thereby reducing production costs.

Despite the potential value of real-time downhole multiphase flow data, the lack of equipment capable of reliable and continuous downhole multiphase flow measurements has severely limited its application. Equipment capable of withstanding harsh operation conditions (e.g., extreme temperatures and pressures), have typically been limited to absolute temperature and pressure sensors. Recently, however, a limited number of techniques have been developed to gather multiphase downhole flow data.

These techniques typically involve downhole mixture density measurements from complex meters (densitometers) that suffer a number of drawbacks, such as nuclear fluid densitometers (NFD). NFDs typically contain complex electronics for performing density measurements that may exhibit reliability and accuracy problems when subjected to downhole operating conditions. Further, because the nuclear densitometers have a radioactive source, due to environmental issues, approvals may be required, and operating personnel may require extensive training.

As an alternative to NFDs, other types of flow meters may be used, such as a Venturi flow meters, designed to correlate measured pressure differences with density measurements to predict individual phase flow rates. However, these devices suffer from a number of disadvantages including restricted access below the device (which may prevent the running of tools below the device) and significant pressure loss due to the restrictive nature of the device. Further, because these devices restrict flow of the mixture, loss of calibration is likely due to erosion and/or accumulation of deposits (e.g., of wax, asphaltenes, etc.). These disadvantages may be compounded by poor resolution and accuracy of pressure sensors used to measure the pressure differences. Overcoming the poor resolution and accuracy may require the use of high contraction ratio (e.g., more restrictive) Venturis.

Accordingly, what is needed is an improved method and apparatus for downhole measurement of flow data of a multiphase mixture.

SUMMARY OF THE INVENTION

Embodiments of the present invention generally provide methods, and apparatus for determining void fractions and flow rates of individual phase components of a multiphase mixture.

For one embodiment, a method for determining one or more volumetric fractions of individual phases of a multiphase mixture flowing through a pipe is provided. The method generally includes measuring a differential pressure between at least two vertically displaced locations along the pipe, measuring a bulk velocity of the mixture and speed of sound in the mixture, and determining a volumetric phase fraction for one or more of the individual phases based on the measured differential pressure, measured bulk velocity of the mixture and measured speed of sound in the mixture.

For one embodiment, a method for determining one or more volumetric fractions of individual phases of a multiphase mixture flowing through a wellbore pipe is provided. The method generally includes measuring a differential pressure between at least two vertically displaced downhole locations along the pipe, measuring a bulk velocity of the mixture and speed of sound in the mixture, and determining a volumetric phase fraction for one or more of the individual phases based on the measured differential pressure, measured bulk velocity of the mixture and measured speed of sound in the mixture. The method may also include measuring a temperature and pressure of the mixture at one or more downhole locations, and estimating densities and speeds of sound for the individual phase components based on the measured temperature and pressure of the mixture.

For some embodiments an apparatus for measuring a volumetric phase fraction of one or more phases of a multiphase mixture in a pipe is provided. The apparatus generally includes a means for sensing differential pressure at two or more vertically displaced locations along the pipe, a velocity sensor for sensing a bulk velocity of the mixture, a speed of sound sensor for sensing a speed of sound in the mixture, and control circuitry. The control circuitry is generally configured to determine a volumetric phase fraction of at least one of the phases based on one or more signals received from the means for sensing differential pressure, the velocity sensor, and the speed of sound sensor. The apparatus may also include an absolute pressure sensor and a temperature sensor. The control circuitry may be further configured to estimate individual phase densities and speeds of sound based on signals received from the absolute pressure sensor and temperature sensor.

BRIEF DESCRIPTION OF THE DRAWINGS

So that the manner in which the above recited features of the present invention, and other features contemplated and claimed herein, are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Embodiments of the present invention generally provide a method, apparatus, and system for determining volumetric fractions of individual phases of a multiphase mixture flowing through a pipe. In general, volumetric fractions and flow rates of the individual phases may be found using a determined mixture density and a measured speed of sound in the mixture. For some embodiments, the mixture density may be determined by direct measurement from a densitometer. For other embodiments, the mixture density may be determined based on a measured pressure difference between two vertically displaced measurement points and a measured bulk velocity of the mixture. Accordingly, such embodiments may utilize various arrangements of non-intrusive pressure sensors, velocity sensors, and speed of sound sensors, thereby overcoming the previously described disadvantages of intrusive devices, such as Venturi flow meters.

As used herein, the term density generally refers to volumetric density and is defined as a mass of a fluid contained within a volume divided by the volume. The terms volumetric phase fraction and void fraction may be used interchangeably and are generally defined as the fractional volume of a mixture occupied by an individual phase component (i.e., the sum of the volumetric phase fractions equals one). As used herein, the term pipe generally refers to any conduit for carrying a fluid (where a fluid is defined as a liquid or a gas). The methods and apparatus described herein may be applied to measure individual phase fractions and flow rates of a wide variety of multiphase mixtures in a wide variety of applications. However, to facilitate understanding, embodiments may be described with reference to measuring individual phase fractions and flow rates of a multiphase mixture of oil, gas, and water, flowing through a wellbore pipe as a specific, but not limiting, application example.

An Exemplary System

Figure 1:
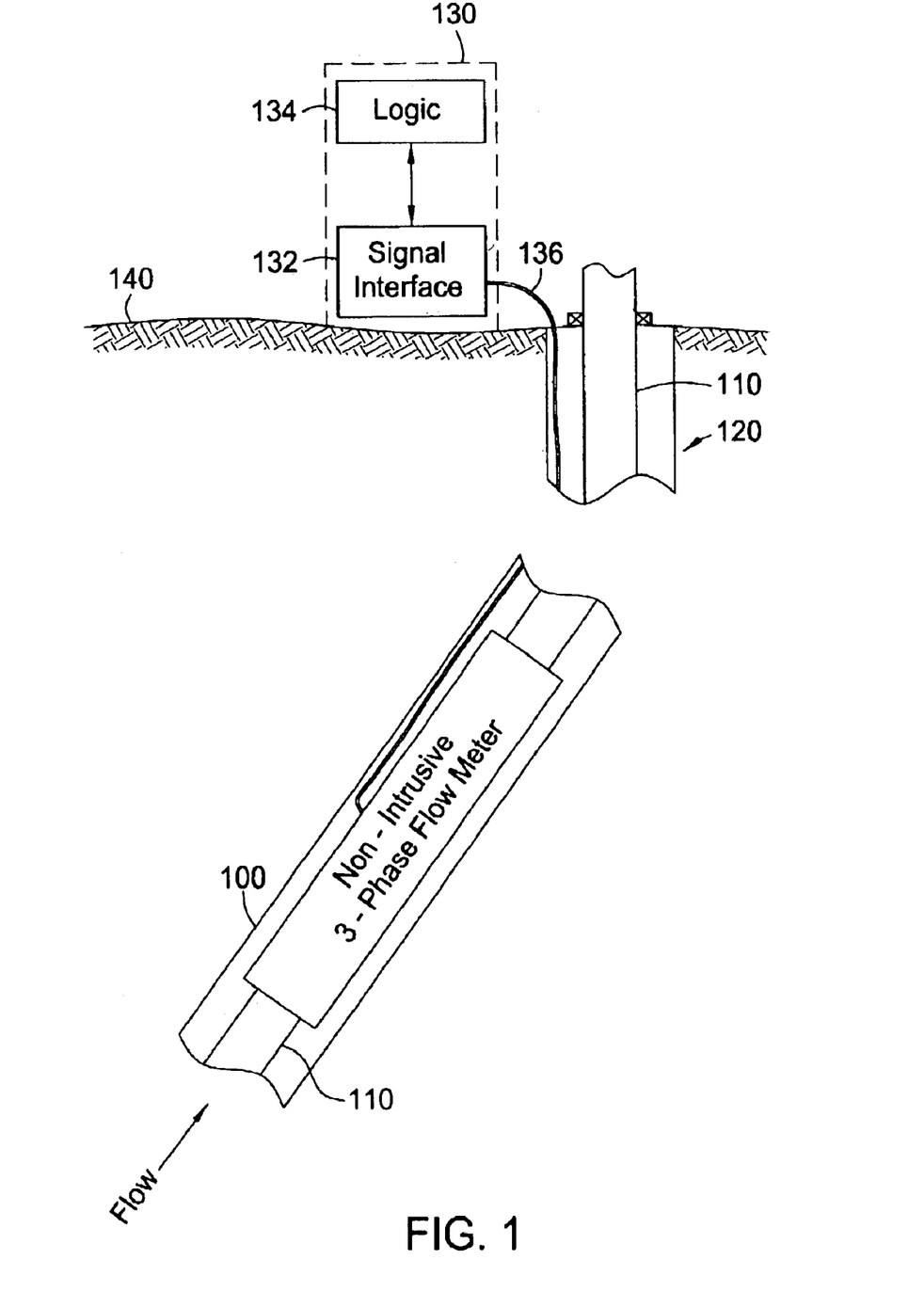
FIG. 1 illustrates an exemplary multiphase measurement system according to one embodiment of the present invention.

FIG. 1 illustrates an exemplary multiphase measurement system, according to one embodiment of the present invention, utilizing a multiphase flow meter 100. As illustrated, the flow meter 100 may be deployed as part of a string of production tubing (pipe) 110 within a wellbore 120 in the stream of flow of a multiphase fluid mixture flowing through the pipe 110. As previously described, the mixture will typically include individual phase components of oil, water, and gas.

For some embodiments, the flow meter 100 may utilize non-intrusive sensors, such that an inner diameter of the flow meter 100 may be equal to or greater than a diameter of sections of pipe 110 upstream and downstream of the flow meter. Accordingly, the flow meter 100 may be capable of operation without restricting the flow of the mixture through the pipe 110. Of course, the flow meter 100 may also be scaled to accommodate pipes 110 of different diameters. Further, as previously described, a plurality of flow meters 100 may be deployed, for example, to monitor flow contributions of multiple zones commingled production, or to identify the location of a production anomaly, such as a gas or water breakthrough.

The flow meter 100 may be monitored by control circuitry 130 located at a surface 140 of the wellbore 120. The control circuitry 130 may include any suitable circuitry responsive to signals generated by the flow meter 100. As illustrated, the control circuitry 130 may include signal interface circuitry 132 and logic circuitry 134. The signal interface circuitry 132 may include any suitable circuitry to receive signals from the flow meter 100 via one or more signal lines 136 and properly condition the signals (e.g., convert the signals to a format readable by the logic circuitry 134).

The logic circuitry 134 may include any suitable circuitry and processing equipment necessary to perform operations described herein. For example, the logic circuitry 134 may include any combination of dedicated processors, dedicated computers, embedded controllers, general purpose computers, programmable logic controllers, and the like. Accordingly, the logic circuitry 134 may be configured to perform operations described herein by standard programming means (e.g., executable software and/or firmware).

The signals generated by the flow meter 100 may be any suitable combination of signals, such as electrical signals, optical signals, or pneumatic signals. Accordingly, the signal lines 136 may be any combination of signal bearing lines, such as electrically conductive lines, optical fibers, or pneumatic lines. Of course, an exact number and type of signal lines 136 will depend on a specific implementation of the flow meter 100.

In general, the flow meter 100 may be configured to generate one or more signals indicative of mixture density and speed of sound in the mixture. For some embodiments, a conventional densitometer may be used to measure mixture density. However, in an effort to overcome the previously described disadvantages associated with conventional densitometers, for other embodiments, mixture density may be determined based on a measured differential pressure between two vertically displaced measurement points and a bulk velocity of the mixture.

Figure 2A:
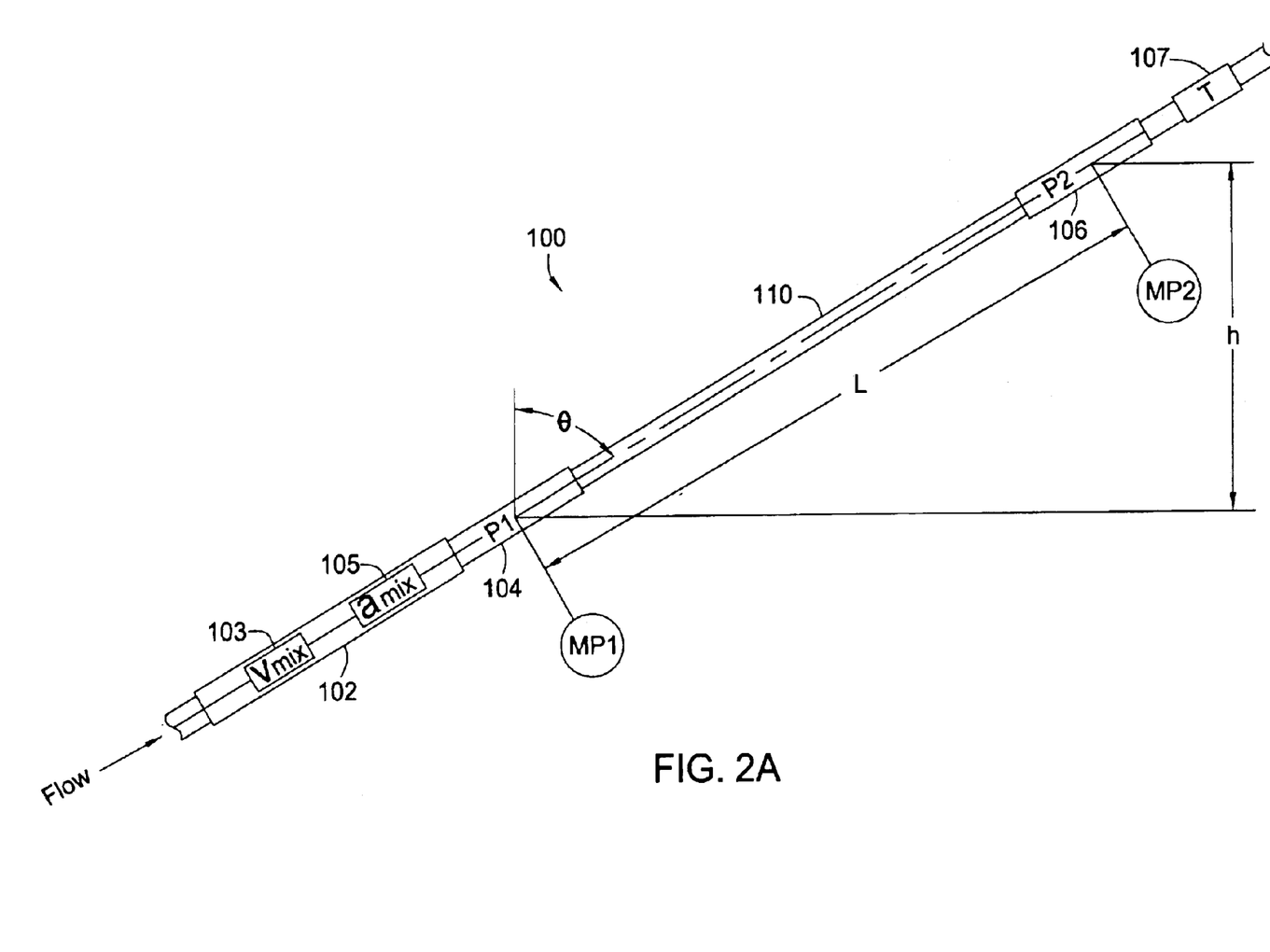
FIGS. 2A–2D are block diagrams of multiphase flow meters according to various embodiments of the present invention.
Figure 2B:
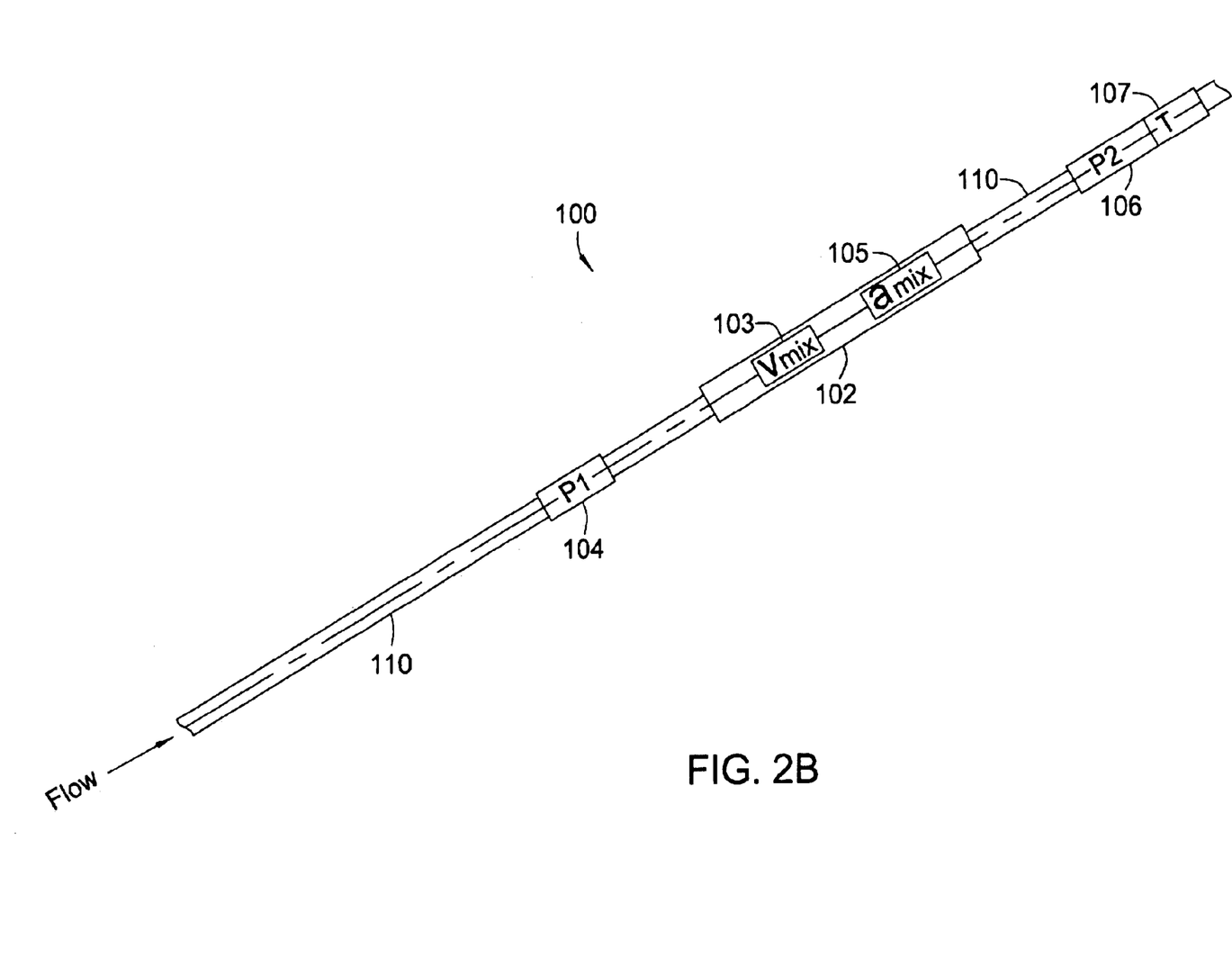
Figure 2C:
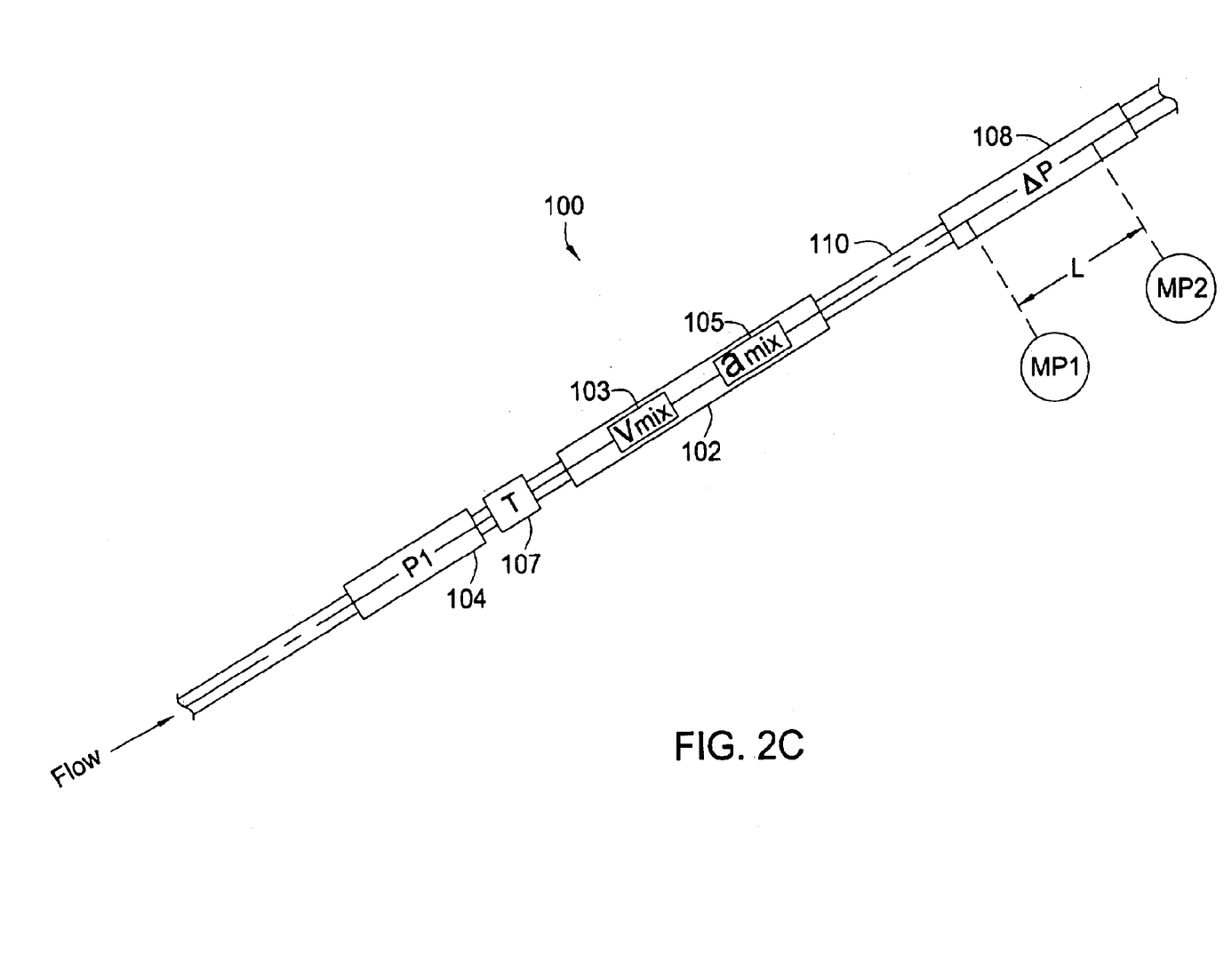
Figure 2D:
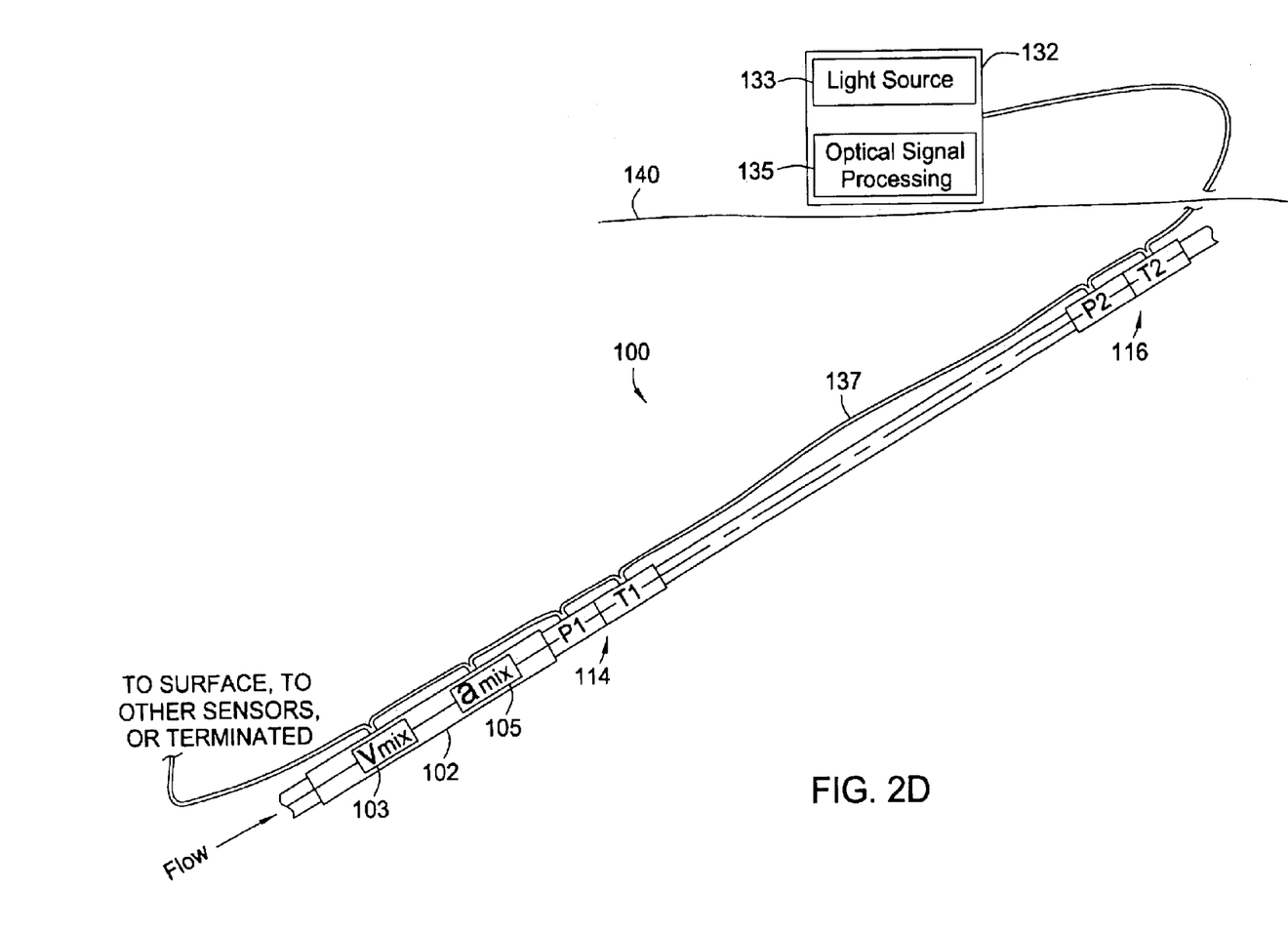

Accordingly, the flow meter 100 may include any suitable arrangement of sensors to measure differential pressure, bulk velocity of the mixture and speed of sound in the mixture. For example, FIGS. 2A–2D illustrate exemplary embodiments of the flow meter 100 with different sensor arrangements capable of measuring differential pressure, bulk velocity, and speed of sound of the mixture. FIG. 2A will be described first to introduce general aspects of the present invention. FIGS. 2B–2D will then be described in greater detail below.

As illustrated in FIG. 2A, the flow meter 100 may include two pressure sensors 104 and 106, displaced vertically by a distance h, for measuring differential pressure between two measurement points, MP1 and MP2, respectively. In other words, the differential pressure between MP1 and MP2 is simply the difference of the pressures measured by the pressure sensor 104 (P1) and the pressure sensor 106 (P2). The vertical displacement h may be determined by the displacement from vertical and the length L between the sensors 104 and 106 (i.e., h=L cos θ). The length L (and/or angle of displacement from vertical θ) may vary with different embodiments and may be chosen such that the vertical displacement h is sufficiently large to provide a hydrostatic pressure difference large enough to overcome accuracy and resolution limitations of the pressure sensors 104 and 106. As illustrated, the flow meter 100 may also include sensors 103 and 105 for measuring bulk velocity ($v_{mix}$) and speed of sound ($\alpha_{mix}$) of the mixture, respectively. As illustrated, the sensors 103 and 105 may be integrated in single flow sensor assembly (FSA) 102.

Determining Mixture Density

In general, the logic circuitry 134 may be configured to determine the volumetric phase fractions for each phase in the mixture based on the differential pressure, bulk velocity, and speed of sound in the mixture measured by the flow meter 100, according to procedures described below, or other similar procedures. As previously described, a density of the mixture may first be determined based on the measured differential pressure and bulk velocity of the mixture. Volumetric phase fractions may then be determined based on the determined mixture density and measured speed of sound in the mixture.

Density of the mixture ($\rho_{mix}$) may be calculated using the measured differential pressure ($\Delta p$) between MP1 and MP2, and measured bulk velocity of the mixture ($v_{mix}$) For example, the pressure drop from MP1 and MP2 is defined by:

$$p_1 - p_2 = \Delta p = \rho_{mix} g h + p_f \quad (1)$$

where the first term is the hydrostatic pressure loss due to gravitational acceleration, while the second term ($p_f$) represents frictional pressure loss. The frictional pressure loss may be estimated using the measured bulk velocity of the mixture and well known frictional loss equations, such as:

$$p_f = \frac{L f \rho_{mix} v_{mix}^2}{2d} \quad (2)$$

where L is the length between the two measurement points, f is the friction factor (e.g., a Moody friction factor calculated using known roughness of an inner surface of the pipe, etc.), and d is the inner diameter of the pipe 110. Substituting Eq. 2 into Eq. 1, and solving for mixture density $\rho_{mix}$ yields:

$$\rho_{mix} = \frac{\Delta p}{gh + \frac{L f v_{mix}^2}{4r}} \quad (3)$$

Thereby, the average density of the mixture $\rho_{mix}$ between MP1 and MP2 may be determined from the measured pressures (P1 and P2) and the bulk velocity of the mixture $v_{mix}$. It should be noted that using Eq. 3, average mixture density $\rho_{mix}$ may be determined independent of the magnitude of slippage in between the different individual phases of the mixture in the pipe.

Determining Volumetric Phase Fractions

Assuming that the mixture flowing through the flow meter 100 is, on average, a homogenous mixture of the individual phases, volumetric fractions of each phase may be calculated on a volumetrically averaged basis. While it is assumed that the fluid mixture moving through the pipe is, on average, a homogeneous mixture of all three phases, no assumptions are made that the three phases are moving at the same velocity.

Accordingly, the volumetric phase fractions may be determined without knowledge of the relative velocities of the individual phases. In fact, on a volumetrically averaged basis, volumetric fractions of either individual phase in the mixture may be determined based on the average (in-situ) mixture density $\rho_{mix}$ (as calculated above) and a speed of sound in the mixture $\alpha_{mix}$, regardless of slippage in between the individual phases.

The mixture density may be expressed in terms of volumetric phase fractions ($\phi_{o,w,g}$) and phase densities ($\rho_{o,w,g}$) of each of the individual phases by the following equation:

$$\rho_{mix} = \phi_o \rho_o + \phi_w \rho_w + \phi_g \rho_g \quad (4)$$

As previously described, the sum of the volumetric fractions equals one:

$$\phi_o + \phi_w + \phi_g = 1 \quad (5)$$

It is known that isentropic compressibility ($\kappa$) of a liquid or gas may be described in terms of density and speed of sound ($\alpha$) in the liquid or gas:

$$\kappa = \frac{1}{\rho a^2} \quad (6)$$

Isentropic compressibility of the mixture ($\kappa_m$) may be expressed in terms of volumetric phase fractions ($\phi_{o,w,g}$) and individual phase compressibilities ($\kappa_{o,w,g}$):

$$\kappa_m = \phi_o \kappa_o + \phi_w \kappa_w + \phi_g \kappa_g \quad (7)$$

As will be described in greater detail below, pure phase speeds of sound ($\alpha_{o,w,g}$) and densities ($\rho_{o,w,g}$) are functions of temperature and pressure and may be determined based on pressure and temperature measurements, for example, from the pressure sensor 106 and a temperature sensor 107, respectively. Thereafter, the individual phase compressibilities ($\kappa_{o,w,g}$) may be readily determined using Eq. 6.

Speed of sound in the mixture $\alpha_{mix}$ may be determined by taking a speed of sound measurement $\alpha_{meas}$ with the speed of sound sensor 105. The speed of sound sensor 105 may measure speed of sound using any suitable technique. For example, the speed of sound sensor 105 may measure speed of sound based on unsteady pressure measurements within the pipe 110. The sensor 105 may "listen" to the propagation of production-generated noise (e.g., caused flow through the pipe 110) across an array of fiber optic based sensors, without the aid of artificial noise source. The unsteady pressure measurements may be obtained at multiple locations within the sensor 105 and provide sufficient spatial and temporal resolution to determine the sound speed of the mixture.

If the speed of sound sensor 105 measures speed of sound based on unsteady pressure in the pipe 110, a correction factor may be required to determine the actual sound speed of the mixture ($\alpha_{mix}$) from the measured sound speed ($a_{meas}$) from the sensor because a pressure pulse propagation through the flow meter 100 will effectively be slowed down due to the compliance of the wall. However, for a circular thin walled pipe (e.g., r>>t) this expression is readily derived and is given by the following equation:

$$a_{meas}^{-2} = a_{mix}^{-2} + \rho_{mix}\frac{2r}{Et} \qquad (8)$$

where the correction factor is the second term the right (r is the radius of the pipe, t is the thickness of the pipe and E is a modulus of elasticity). Dividing both sides of Eq. 8 by $\rho_m$, rearranging, and substituting Eq. 6 yields:

$$\frac{1}{\rho_{mix}a_{mix}^2} = \kappa_{mix} = \frac{1}{\rho_{mix}a_{meas}^2} - \frac{2r}{Et} \qquad (9)$$

In other words, the mixture compressibility may be determined based on the mixture density ($\rho_{mix}$), calculated from the hydrostatic pressure difference above, and the speed of sound ($\alpha_{meas}$) in the pipe measured by the speed of sound sensor 105. Of course, the correction factor may not be required if mixture speed of sound is measured using other types of speed of sound sensors, such as ultrasonic speed of sound sensors.

Using the mixture compressibility and density, volumetric fractions of the individual phases may be determined as follows. Eq. 5 may be rewritten to express any individual phase in terms of the other individual phases (e.g., $\phi_g=1-\phi_o-\phi_w$). Substituting rewritten Eq. 5 into Eqs. 4 and 7 yields the following equations:

$$\rho_{mix}=\phi_o\rho_o+\phi_w\rho_w+(1-\phi_o-\phi_w)\rho_g \qquad (10)$$

$$\kappa_{mix}=\phi_o\kappa_o+\phi_w\kappa_w+(1-\phi_o-\phi_w)\kappa_g \qquad (11)$$

which may be solved for the oil fraction ($\phi_o$) or the water fraction ($\phi_w$). For example, solving Eqs. 10 and 11 for water fraction yields:

$$\phi_w = \frac{\phi_o(\rho_g - \rho_o) + \rho_{mix} - \rho_g}{\rho_w - \rho_g} \qquad (12)$$

$$\phi_w = \frac{\phi_o(\kappa_g - \kappa_o) + \kappa_{mix} - \kappa_g}{\kappa_w - \kappa_g} \qquad (13)$$

Eqs. 12 and 13 may be equated, and solved for oil fraction, which yields:

$$\phi_o = \frac{(\kappa_{mix} - \kappa_g)(\rho_w - \rho_g) - (\kappa_{mix} - \kappa_g)(\rho_{mix} - \rho_g)}{(\kappa_w - \kappa_g)(\rho_g - \rho_o) - (\kappa_g - \kappa_o)(\rho_w - \rho_g)} \qquad (14)$$

Eq. 14 is an explicit expression of the oil volume fraction in a measurement section of the flow meter 100 in terms of mixture density and mixture compressibility (which is readily found from Eq. 9 based on the measured speed of sound in the mixture). The oil fraction determined by Eq. 14 may then be used with Eq. 12 to determine the water fraction, and gas fraction may be found from Eq. 5, using the oil fraction and water fraction.

Of course, solving for the oil phase fraction first in the example above was arbitrary and equations of the same form as Eq. 14 may also be found for both the gas and water phase fraction:

$$\phi_g = \frac{(\kappa_{mix} - \kappa_w)(\rho_o - \rho_w) - (\kappa_o - \kappa_w)(\rho_{mix} - \rho_w)}{(\kappa_o - \kappa_w)(\rho_w - \rho_g) - (\kappa_w - \kappa_g)(\rho_o - \rho_w)} \qquad (15)$$

$$\phi_w = \frac{(\kappa_{mix} - \kappa_g)(\rho_o - \rho_g) - (\kappa_o - \kappa_g)(\rho_{mix} - \rho_g)}{(\kappa_o - \kappa_g)(\rho_g - \rho_w) - (\kappa_g - \kappa_w)(\rho_o - \rho_g)} \qquad (16)$$

Further, for some embodiments, only some, rather than all, of the volumetric phase fractions may be determined. Regardless, embodiments of the present invention provide for simplified determination of volumetric fractions of individual phases based on measured parameters of the mixture, as a whole.

Sensor Arrangements

As previously described, the flow meter 100 may include any suitable arrangement of sensors capable of measuring the mixture parameters (e.g., differential pressure, bulk velocity, and speed of sound) for use in determining volumetric phase fractions. The sensor arrangement of FIG. 2A is illustrative of just one suitable arrangement, and may be modified in various ways. For example, while the FSA 102 may be located below the pressure sensor 104, as shown in FIG. 2A, it may also be located above the pressure sensor 106, or between the pressure sensors 104 and 106, as shown in FIG. 2B. Of course, while the velocity sensor 103 and speed of sound sensor 105 are shown as part of the FSA 102, the sensors 103 and 105 may alternatively be separate sensors.

Further, as illustrated in FIG. 2C, a single differential pressure sensor 108, rather than separate absolute pressure sensors 104 and 106, may be utilized to provide a single differential pressure signal, as illustrated in FIG. 2C. An advantage to the differential pressure sensor 108 is that the distance L between measurement points (MP1 and MP2) may be more accurately controlled than with separate pressure sensors 104 and 106. Of course, accurate information regarding the displacement from vertical is still necessary to determine vertical displacement of measurement points (h) for use in Eq. 3 to determine the mixture density. As illustrated, an absolute pressure sensor 106 and temperature sensor 107 may still be provided, in addition to the differential pressure sensor 108, to allow determination of individual phase densities and speeds of sound, as will be described in greater detail below.

Regardless of the particular arrangement, the various sensors utilized in the flow meter 100 may be any combination of suitable sensors. As an example, the velocity sensor 103 may be similar to those described in commonly-owned U.S. Pat. No. 6,463,813, entitled "Displacement Based Pressure Sensor Measuring Unsteady Pressure in a Pipe", issued Oct. 15, 2002 and incorporated herein by reference. As another example, the pressure sensors 104–108 may be any suitable type of strain sensors, quartz sensors, piezoelectric sensors, etc. Due to harsh operating conditions (e.g., elevated temperatures, pressures, mechanical shock, and vibration) that may exist downhole, however, accuracy and resolution of conventional electronic sensors may degrade over time.

Fiber optic sensors offer one alternative to conventional electronic sensors. Typically, fiber optic sensors have no downhole electronics or moving parts and, therefore, may be exposed to harsh downhole operating conditions without the typical loss of performance exhibited by electronic sensors. Accordingly, for some embodiments, one or more of the sensors utilized in the flow meter 100 may be fiber optic sensors.

For example, as illustrated in FIG. 2D, the flow meter 100 may include fiber optic sensors (e.g., sensors 114–116 and sensors 103 and 105 within FSA 102) which utilize strain-sensitive Bragg gratings (not shown) formed in a core of one or more optical fibers 137 (e.g., the signal lines 136 of FIG. 1 may include one or more optical fibers 137). As illustrated, the sensors 114 and 116 may be combination pressure and temperature (P/T) sensors, similar to those described in detail in commonly-owned U.S. Pat. No. 5,892,860, entitled "Multi-Parameter Fiber Optic Sensor For Use In Harsh Environments", issued Apr. 6, 1999 and incorporated herein by reference. Further, for some embodiments, the flow meter 100 may utilize a fiber optic differential pressure sensor (not shown). The velocity sensor 103 and speed of sound sensor 105 of FSA 102 may be similar to those described in commonly-owned U.S. Pat. No. 6,354,147, entitled "Fluid Parameter Measurement In Pipes Using Acoustic Pressures", issued Mar. 12, 2002 and incorporated herein by reference. Bragg grating-based sensors are suitable for use in very hostile and remote environments, such as found downhole in wellbores.

As illustrated, to interface with fiber optic sensors, the signal interface 132 may include a broadband light source 133, such as a light emitting diode (LED), and appropriate equipment for delivery of signal light to the Bragg gratings formed within the core of the optical fibers 137. Additionally, the signal interface 132 may include appropriate optical signal processing equipment 135 for analyzing the return signals (reflected light) from the Bragg gratings (and converting the return signals into signals compatible with the logic circuitry 134).

Depending on a specific arrangement, the fiber optic sensors may be distributed on a common one of the fibers 137 or distributed among multiple fibers. As illustrated, the fibers 137 may be connected to other sensors (e.g., further downhole), terminated, or connected back to the signal interface 132. Accordingly, while not shown, the flow meter 100 of FIG. 2D may also include any suitable combination of peripheral elements (e.g., fiber optic cable connectors, splitters, etc.) well known in the art for coupling the fibers 137. Further, the fibers 137 may be encased in protective coatings, and may be deployed in fiber delivery equipment, as is also well known in the art.

Figure 3:
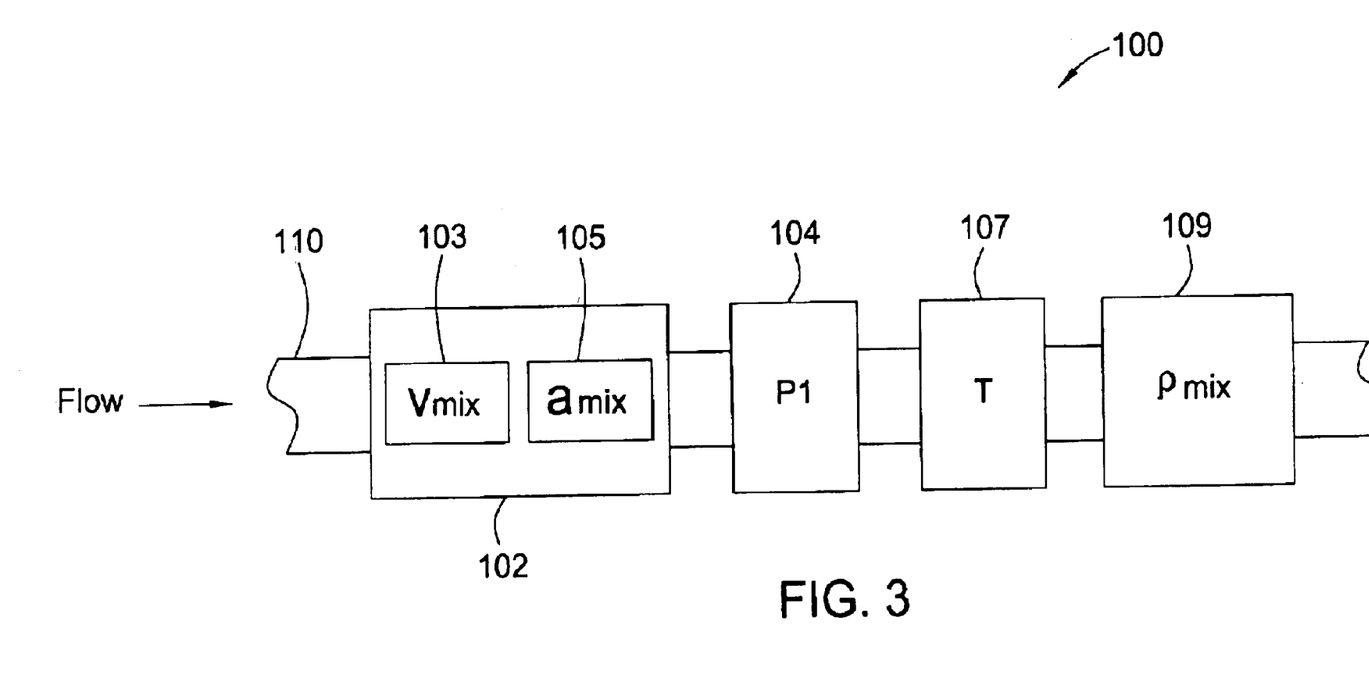
FIG. 3 is a block diagram of a multiphase flow meter, according to the present invention, utilizing a conventional densitometer.

While the FIGS. 2A–2D illustrate exemplary sensor arrangements capable of measuring mixture density based on hydrostatic pressure differences, as previously described, mixture density may also be measured using a densitometer 109, as illustrated in FIG. 3, thus eliminating the need to use Eq. 3 above. The densitometer 109 may be any suitable densitometer (e.g., a nuclear fluid densitometer). As illustrated, the densitometer 109 may be oriented horizontally, as a hydrostatic pressure difference is not required to measure the mixture density. Operation of the remaining illustrated elements is as described above. In other words, pure phase densities and speeds of sound may still be calculated based on absolute temperature and pressure measurements from sensors 104 and 107, respectively, while mixture speed of sound may be measured with speed of sound sensor 105. Mixture bulk velocity, while not required for determining mixture density in this arrangement, may still be measured by sensor 103, for example, for determination of individual phase flow rates.

An Exemplary Algorithm

Regardless of the particular arrangement of sensors, the flow meter 100 is generally configured to communicate signals indicative of mixture density (directly, or via differential pressure measurements), bulk velocity of the mixture, and speed of sound in the mixture, to the control circuitry 130 at the surface 140. The signals are then processed by the signal processing circuitry 132 and communicated to the logic circuitry 134 which may be generally configured to perform any suitable algorithms to determine volumetric phase fractions according to the procedures described above.

Figure 4:
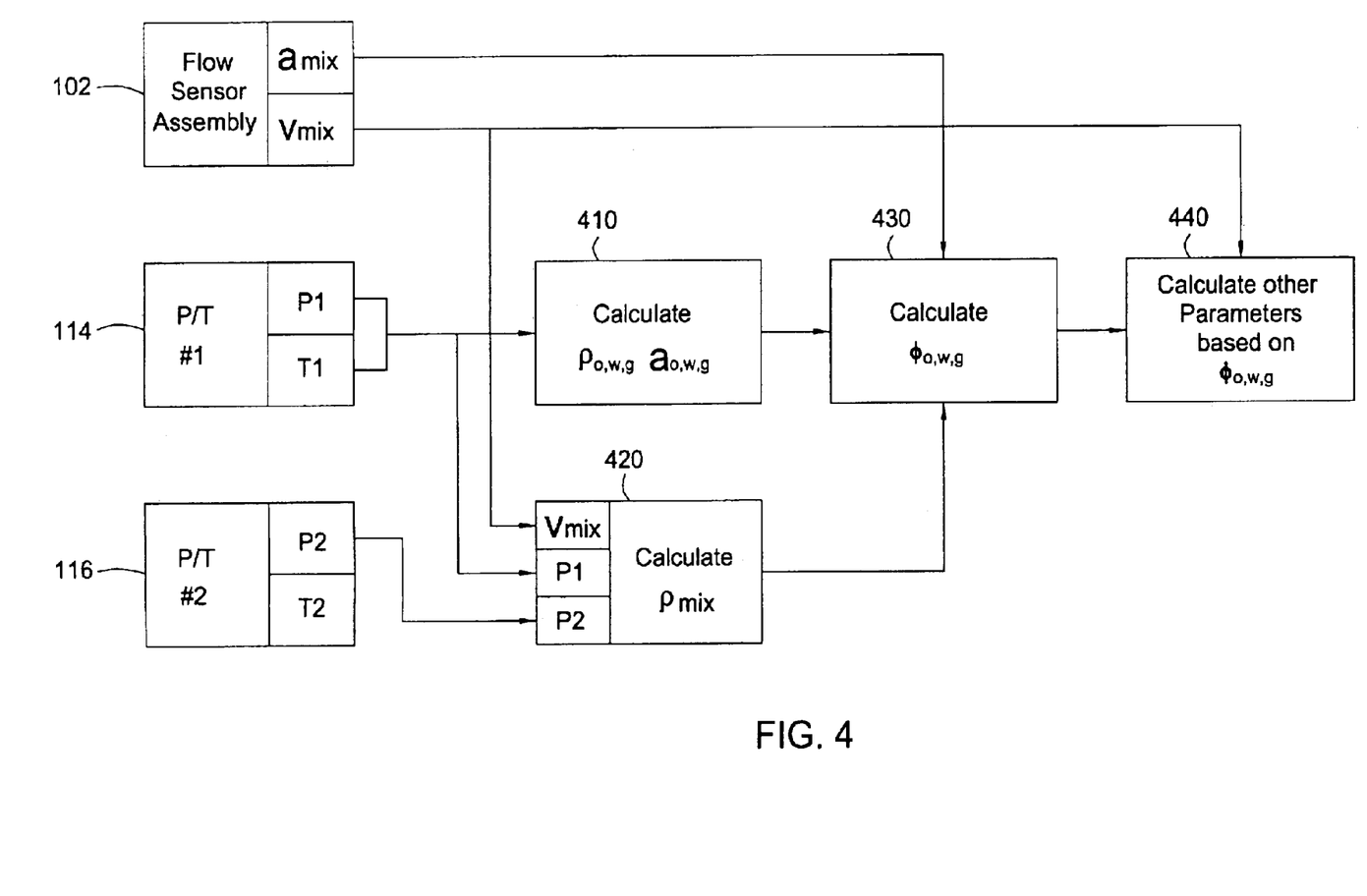
FIG. 4 is a functional block diagram of a multiphase flow meter according to an embodiment of the present invention.

FIG. 4 is a functional block diagram that illustrates the flow of the various sensor measurements and calculations, according to one embodiment of the present invention. The calculations of blocks 410–440 may be performed (e.g., by logic circuitry 134) as part of a set of operations 400, shown in FIG. 5, for determining volumetric phase fractions. Accordingly, the operations 400 of FIG. 5, and the block diagram of FIG. 4 may be best described concurrently. While the operations 400 include operations (412 and 420) for measuring differential pressure and determining mixture density based on the measured differential pressure, these operations may be omitted if measuring mixture density directly, for example, with a densitometer.

Figure 5:
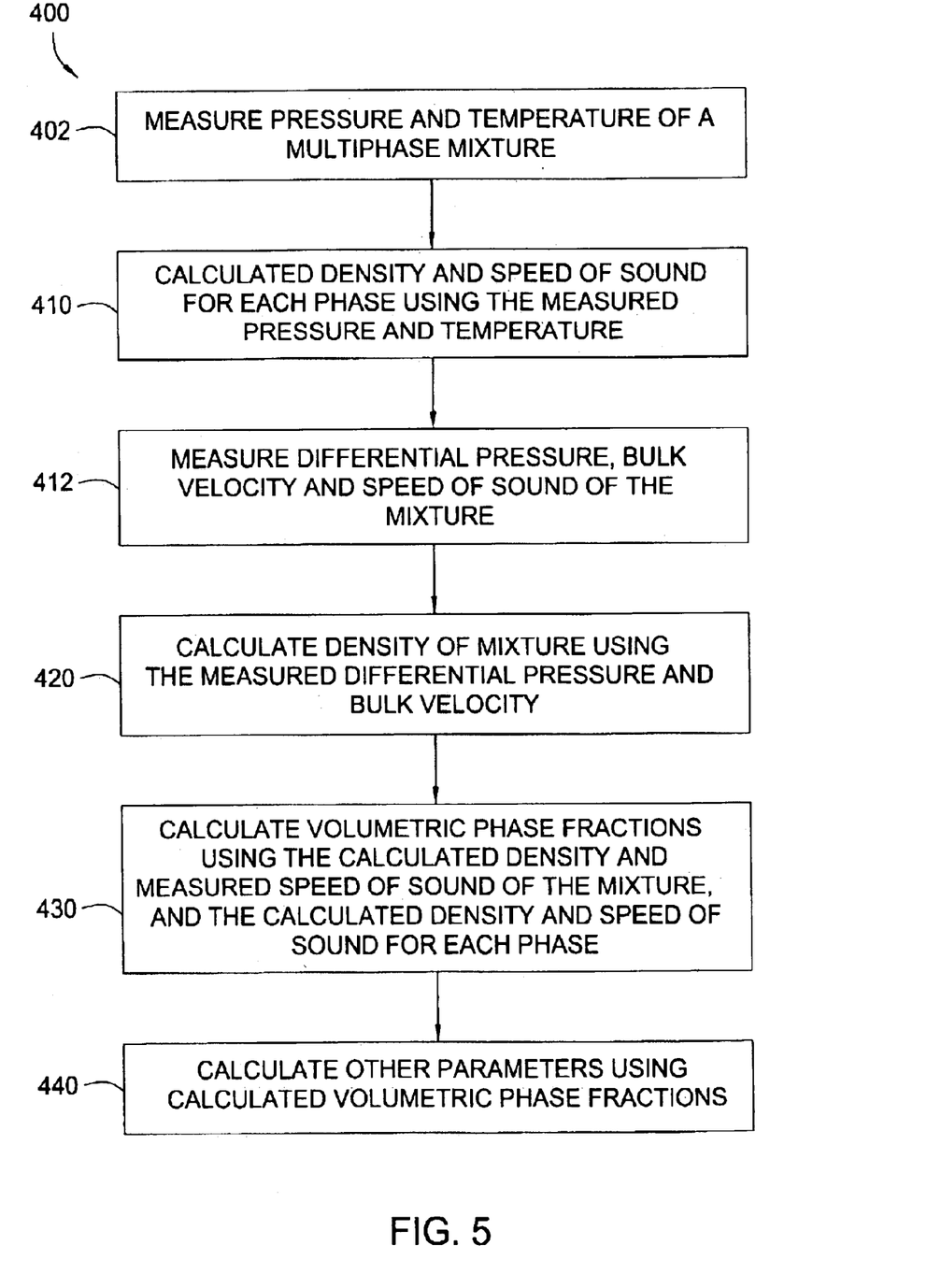
FIG. 5 is a flow diagram illustrating exemplary operations for determining volumetric fractions of individual phases of a multiphase mixture according to an embodiment of the present invention.

At step 402, pressure and temperature of the mixture are measured. At step 410, individual phase densities $\rho_{o,w,g}$ and speeds of sound $\alpha_{o,w,g}$ are calculated based on the measured pressure and temperature. As described above, the individual phase densities and speeds of sound may be used later (e g., in Eq. 14–16) in determining the volumetric phase fractions. The individual phase densities and speeds of sound may be calculated using any suitable algorithm. For example, the logic circuitry 134 may be configured to access a table or file of parameters (equation coefficients, lookup tables, etc.) for use in calculating the individual phase densities and speeds of sound from the measured pressure and temperature. Once the individual phase densities and speed of sound are determined, the individual compressibilities $\kappa_{o,w,g}$ may also be determined using Eq. 6.

As illustrated, the pressure and temperature measurements may be provided by the combination pressure/temperature sensor 114. Of course, separate pressure and temperature sensors may also be used. While the temperature and pressure measurements may be indicative of the temperature and pressure of the individual phases at one point along the flow meter 100, density and speed of sound calculations using the measurements may be sufficient because absolute temperature and pressure downhole is typically relatively high. In other words, relatively small changes in temperature and pressure within the flow meter 100 may not result in significant changes in the individual phase densities and speeds of sound. However, because the absolute pressure and temperature of the mixture may change in time, the operations of steps 402 and 410 may be repeated, as necessary, to update the individual phase densities, speeds of sound, and compressibilities $(\rho_{o,w,g}, \alpha_{o,w,g}, \kappa_{o,w,g})$.

At step 412, the differential pressure, bulk velocity, and speed of sound of the mixture is measured and used to calculate the mixture density, at step 420 (e.g., using Eq. 3, above). As previously described, the differential pressure may be provided by two pressure sensors (e.g., P/T sensors 114 and 116, as illustrated) or a single differential pressure sensor (e.g., sensor 108 shown in FIG. 2C). Similarly, the bulk velocity and speed of sound of the mixture may be provided by the sensors 103 and 105, which may be separate sensors, or integrated with the FSA 102, as shown.

At step 430, the volumetric phase fractions are calculated using the calculated mixture density, measured speed of sound in the mixture, and the calculated individual phase densities and speeds of sound. For example, the individual volumetric phase fractions may be determined, in any order, using the Eq. 14–16. As an intermediate step, the compressibility of the mixture may be determined, using Eq. 8, from mixture density and measured speed of sound in the mixture.

Of course, the calculations and equations described above may be consolidated in various ways to eliminate intermediate calculations. As an example, Eqs. 3 and 9 may be substituted into Eqs. 14–16 to calculate volumetric phase fractions without the intermediate calculation of mixture density. Accordingly, the exact equations, and order of equations used to determine volumetric phase fractions and/or any other parameter derived from the volumetric phase fractions may be an implementation specific decision.

Other Multiphase Parameters

At step 440, other parameters may optionally be calculated using the previously calculated volumetric phase fractions. For example, those skilled in the art will realize that various other useful parameters are functions of the individual volumetric phase fractions including, but not limited to, liquid holdup, watercut, and individual phase flow rates. Liquid holdup and watercut are common parameters used to monitor production.

Liquid holdup generally refers to the percentage of liquid phase content (combined oil and water phases) of the mixture. Liquid holdup may be defined in terms of the volumetric phase fractions as:

$$HL = \frac{\phi_o + \phi_w}{\phi_o + \phi_w + \phi_g} = \phi_o + \phi_w \quad (17)$$

Watercut generally refers to the amount of water in the liquid (oil and water) phase of the mixture. Watercut may be defined in terms of the volumetric phase fractions as:

$$WC = \frac{\phi_w}{\phi_o + \phi_w} = \frac{\phi_w}{HL} \quad (18)$$

In other words, liquid holdup ranges from 0 for a pure gas phase to 1 for a pure liquid phase while watercut ranges from 0 for a mixture with no water to 1 for a mixture with no oil.

Figure 6:
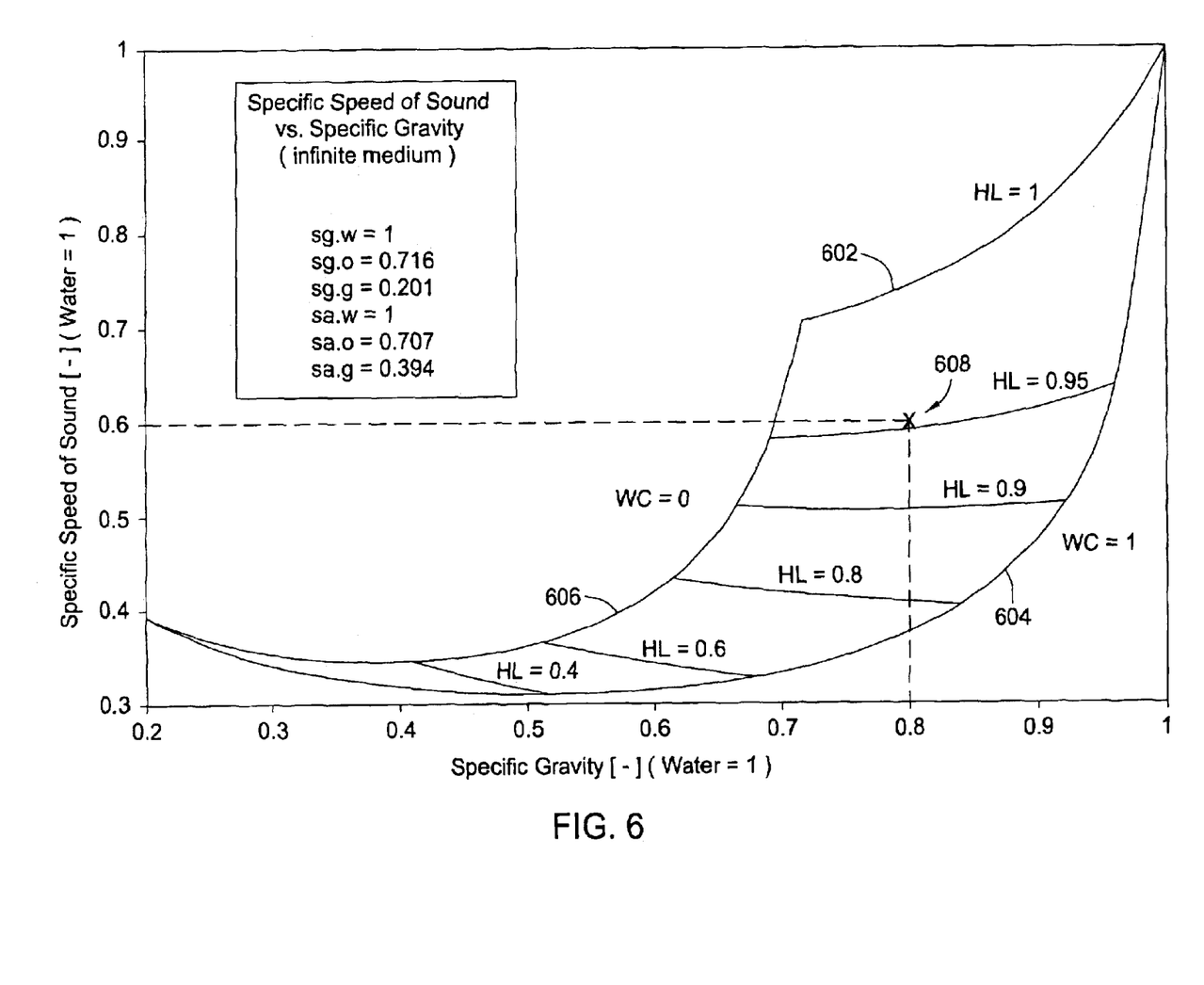
FIG. 6 is a graph that illustrates an envelope of possible density and speed of sound measurements in a mixture.

A graphical representation of liquid holdup and watercut is shown in FIG. 6. The graph of FIG. 6 may be constructed by substituting Eq. 17 and 18 into Eq. 10 and 11, and solving the equations to yield an expression relating the mixture speed of sound to the mixture density with watercut and liquid holdup as parameters. This expression may then be solved for different values of watercut and liquid holdup, to generate the illustrated graph.

The graph illustrates an envelope of measured speed of sound (normalized to speed of sound in water=1) and mixture density (normalized to specific gravity of water=1). Pure phase states are defined by the intersections of lines 602, 604, and 606, which represent a liquid holdup of 1, a watercut of 1, and a watercut of 0, respectively. In other words, the intersection of lines 604 and 606 (lower left) corresponds to a pure gas phase (HL=0), the intersection of lines 604 and 602 (upper right) corresponds to a pure water phase (HL=1, WC=1), and the intersection of lines 602 and 606 corresponds to a pure oil phase (HL=1, WC=0).

The graph of FIG. 6 may be used as a quick reference to quickly determine mixture properties in terms of watercut and liquid holdup. For example, point 608 represents an exemplary measurement from the flow meter 100, corresponding to a speed of sound measurement for the mixture of approximately 0.6 and a calculated mixture density of approximately 0.8. As illustrated, the measured point 608 corresponds to a liquid holdup of about 95% and a watercut of approximately 50%. Of course, exact values of individual phases can always be calculated using equations 14, 12, and 5, described above.

Total volumetric flow rate of the mixture may be calculated using the measured bulk velocity of the mixture:

$$Q_{tot} = v_{mix} A \quad (19)$$

where A is the total cross-sectional measurement area of the flow meter through which the mixture is flowing. The total flow rate of the mixture may be combined with the calculated mixture density to determine mass flow rate:

$$n_{tot} = Q_{tot} \rho_{mix} = v_{mix} A \rho_{mix} \quad (20)$$

Using these (volumetric and mass) flow rates for the total mixture, flow rates for the individual phases may also be calculated. For example, flow rates of the individual phases may be calculated based on the previously calculated volumetric phase fractions and the measured bulk velocity using well known multiphase flow models. A particular multiphase flow model used may depend on application specific details (e.g., various measurements, calculations, and/or assumptions regarding individual phase components of the mixture). The application of specific multiphase flow models is well known and, further, commercial software packages are available that facilitate application of multiphase flow models.

Conclusion

While the foregoing description has primarily focused on determining volumetric phase fractions (and associated derivative parameters), of oil, gas, and water in a multiphase mixture flowing through a wellbore pipe, embodiments of the present invention may generally be applied to determine volumetric fractions, volumetric flow rates, and mass flow rates of individual phases of any type multiphase mixture. By determining individual volumetric phase fractions from measured mixture parameters (e.g., mixture density and speed of sound), complex equipment required to directly measure individual phase fractions and flow rates may be avoided. For some embodiments, mixture density measurements may be taken using fiber-optic based differential pressure and bulk velocity measurements, eliminating the need for complex densitometers (e.g., nuclear fluid densitometers). Further, by utilizing non-intrusive fiber optic sensors for measuring the mixture parameters, a highly reliable and accurate multiphase flow meter may be provided without the disadvantages of intrusive flow meters, such as loss of calibration due to erosion/buildup and loss of pressure. Further, by maintaining a full wellbore, a non-intrusive flow meter may provide access to run tools below the flow meter.

While the foregoing is directed to embodiments of the present invention, other and further embodiments of the invention may be devised without departing from the basic scope thereof, and the scope thereof is determined by the claims that follow.

What is claimed is:

1. A method for determining one or more volumetric fractions of individual phases of a multiphase mixture flowing through a pipe, comprising:

measuring one or more parameters collectively indicative of a density of the mixture, comprising:
   measuring a differential pressure between two locations along the pipe; and
   measuring a bulk velocity of the mixture;
measuring a speed of sound in the mixture;
determining a density of the mixture comprising determining the density based on the measured differential pressure and the measured bulk velocity and estimating an amount of frictional loss based on the bulk velocity; and
using control circuitry to determine a volumetric phase fraction for one or more of the individual phases based on the one or more parameters collectively indicative of the mixture density and the measured speed of sound in the mixture.

2. The method of claim 1, further comprising;
measuring a temperature and pressure of the mixture; and
estimating densities and speeds of sound for the individual phases based on the measured temperature and pressure of the mixture.

3. The method of claim 2, wherein the estimated densities and speeds of sound for the individual phases are used in determining the volumetric phase fraction for the one or more of the individual phases.

4. The method of claim 1, further comprising determining a percentage amount of liquid phase content of the mixture based on the determined volumetric phase fractions.

5. The method of claim 1, further comprising determining a volumetric flow rate for one or more of the individual phases based on the determined volumetric phase fractions by applying a multiphase flow model.

6. A method for determining one or more volumetric fractions of individual phases of a multiphase mixture flowing through a pipe, comprising:
   measuring a differential pressure between at least two vertically displaced locations along the pipe;
   measuring a bulk velocity of the mixture and speed of sound in the mixture;
   determining a density of the mixture based on the measured differential pressure and measured bulk velocity of the mixture comprising estimating an amount of frictional loss based on the measured bulk velocity of the mixture; and
   using control circuitry to determine a volumetric phase fraction for one or more of the individual phases based on the measured differential pressure, measured bulk velocity of the mixture and measured speed of sound in the mixture.

7. The method of claim 6, further comprising determining a volumetric flow rate for one or more of the individual phases, or a combination of individual phases, based on the determined volumetric phase fractions by applying a multiphase flow model.

8. The method of claim 6, wherein the pipe is a wellbore pipe within a wellbore.

9. A method for determining one or more volumetric fractions of individual phases of a multiphase mixture flowing through a pipe, comprising:
   measuring a differential pressure between at least two vertically displaced locations along the pipe;
   measuring a bulk velocity of the mixture and speed of sound in the mixture;
   determining a density of the mixture based on the measured differential pressure and measured bulk velocity of the mixture; and
   using control circuitry to determine a volumetric phase fraction for one or more of the individual phases based on the measured differential pressure, measured bulk velocity of the mixture and measured speed of sound in the mixture, comprising determining the volumetric phase fraction for one of the individual phases as a function of the determined density of the mixture, estimated density of the individual phases, and estimated speed of sound in the individual phases.

10. A method for determining one or more volumetric fractions of individual phase components of a multiphase mixture flowing through a pipe, comprising:
    measuring a temperature and pressure of the mixture at one or more locations;
    estimating densities and speeds of sound for the individual phase components based on the measured temperature and pressure of the mixture;
    measuring a differential pressure between at least two vertically displaced locations along the pipe;
    measuring a bulk velocity of the mixture and speed of sound in the mixture; and
    using control circuitry to determine a volumetric phase fraction for one or more of the individual phase components based on the estimated densities and speeds of sound for the individual phase components, the measured differential pressure, the measured bulk velocity of the mixture, and the measured speed of sound in the mixture.

11. The method of claim 10, wherein measuring the differential pressure between the at least two vertically displaced locations comprises measuring absolute pressures at each of the at least two vertically displaced locations.

12. The method of claim 10, wherein measuring a temperature of the mixture at one or more locations comprises detecting temperature induced changes in an optical fiber.

13. The method of claim 10, wherein measuring the temperature and pressure of the mixture at one or more locations comprises measuring the temperature and pressure of the mixture using one or more fiber optic based sensors.

14. The method of claim 10, wherein measuring the bulk velocity of the mixture and speed of sound in the mixture comprises measuring the bulk velocity of the mixture and speed of sound in the mixture using one or more fiber optic based sensors.

15. The method of claim 14, wherein the one or more fiber optic based sensors are non-intrusive.

16. The method of claim 10, further comprising determining a liquid holdup value for the mixture based on the one or more determined volumetric phase fractions.

17. The method of claim 10, further comprising determining a watercut value for the mixture based on the one or more determined volumetric phase fractions.

18. The method of claim 10, wherein the pipe is a wellbore pipe within a wellbore.

19. An apparatus for measuring a volumetric phase fraction of one or more phases of a multiphase mixture in a pipe, comprising:
    a means for sensing differential pressure at two or more vertically displaced locations along the pipe;
    a velocity sensor for sensing a bulk velocity of the mixture;
    a speed of sound sensor for sensing a speed of sound in the mixture;
    control circuitry adapted to determine a volumetric phase fraction of at least one of the phases based on one or more signals received from the means for sensing differential pressure, the velocity sensor, and the speed of sound sensor; and at least one temperature sensor, wherein the control circuitry is further adapted to determine a speed of sound and density of each of the phases based on one or more signals received from the temperature sensor and an absolute pressure sensor.

20. The apparatus of claim 19, wherein the means for measuring differential pressure comprises at least two absolute pressure sensors disposed at the two or more vertically displaced locations along the pipe.

21. The apparatus of claim 19, wherein the temperature sensor and absolute pressure sensor form an integrated sensor.

22. The apparatus of claim 19, wherein an inner diameter of the apparatus is equal to or greater than an inner diameter of the pipe on at least one end of the apparatus.

23. The apparatus of claim 19, wherein the control circuitry is further configured to determine a volumetric flow rate for at least one of the phases by applying a multiphase flow model.

24. The apparatus of claim 19, wherein the control circuitry is further configured to determine a percentage amount of liquid phase content of the mixture.

25. The apparatus of claim 19, wherein the pipe is a wellbore pipe within a wellbore.

26. An apparatus for measuring a volumetric fraction of one or more phase components of a multiphase mixture in a pipe, comprising an absolute pressure sensor;

a temperature sensor;

a means for sensing differential pressure at two or more vertically displaced locations along the pipe;

a velocity sensor for sensing a bulk velocity of the mixture;

a speed of sound sensor for sensing a speed of sound in the mixture; and control circuitry configured to estimate individual phase densities and speeds of sound based on signals received from the absolute pressure sensor and temperature sensor, and to determine a volumetric fraction of at least one of the phase components based on one or more signals received from the means for sensing differential pressure, the velocity sensor, and the speed of sound sensor, and the estimated individual phase densities and speeds of sound.

27. The apparatus of claim 26, wherein the control circuitry is configured to calculate a density of the mixture based on one or more signals received from the means for sensing differential pressure and the velocity sensor prior to determining the volumetric fraction of at least one of the phase components.

28. The apparatus of claim 26, wherein the control circuitry is located at a surface of a wellbore.

29. The apparatus of claim 26, wherein the means for sensing differential pressure comprises two fiber optic based absolute pressure sensors, each comprising one or more Bragg gratings.

30. The apparatus of claim 29, wherein the temperature sensor is integrated with one of the pressure sensors.

31. The apparatus of claim 29, wherein the temperature sensor, the means for sensing differential pressure, the velocity sensor, and the speed of sound sensor comprise one or more fiber optic sensors coupled with the control circuitry via one or more optical fibers.

32. The apparatus of claim 31, wherein each of the one or more fiber optic sensors are coupled with the control circuitry via a common optical fiber.

33. The apparatus of claim 26, wherein the control circuitry is configured to calculate a watercut parameter based on determined volumetric fractions of oil and water in the mixture.

34. The apparatus of claim 26, wherein the control circuitry is configured to calculate a liquid holdup parameter based on determined volumetric fractions of oil and water in the mixture.

35. The apparatus of claim 26, wherein at least one of the temperature sensor, the means for sensing differential pressure, the velocity sensor, and the speed of sound sensor is an electrical sensor.

36. The apparatus of claim 26, wherein the pipe is a wellbore pipe within a wellbore.

* * * * *